US009844216B2

(12) United States Patent
Grascha et al.

(10) Patent No.: US 9,844,216 B2
(45) Date of Patent: Dec. 19, 2017

(54) CHEMICAL COMPOSITION WITH HYDROGEN PEROXIDE AND A NANOEMULSION OF LONG-CHAINED ALCOHOLS

(75) Inventors: Pierre Grascha, Cormontreuil (FR); Mylène Battut, La Norville (FR)

(73) Assignee: Deb IP Limited, Derbyshire (GB)

( * ) Notice: Subject to any disclaimer, the term of this patent is extended or adjusted under 35 U.S.C. 154(b) by 266 days.

(21) Appl. No.: 14/002,432

(22) PCT Filed: Mar. 2, 2011

(86) PCT No.: PCT/EP2011/053100
§ 371 (c)(1),
(2), (4) Date: Nov. 27, 2013

(87) PCT Pub. No.: WO2012/116744
PCT Pub. Date: Sep. 7, 2012

(65) Prior Publication Data
US 2014/0086968 A1    Mar. 27, 2014

(51) Int. Cl.
| | |
|---|---|
| *A61K 8/02* | (2006.01) |
| *A01N 25/00* | (2006.01) |
| *A61K 9/00* | (2006.01) |
| *A61K 9/107* | (2006.01) |
| *A61K 47/10* | (2017.01) |
| *A61K 47/26* | (2006.01) |
| *A61K 31/05* | (2006.01) |
| *A61K 31/07* | (2006.01) |
| *A61K 33/40* | (2006.01) |
| *A01N 59/00* | (2006.01) |
| *A61Q 17/00* | (2006.01) |
| *A61K 8/06* | (2006.01) |
| *A61K 8/22* | (2006.01) |

(52) U.S. Cl.
CPC ............ *A01N 25/00* (2013.01); *A01N 59/00* (2013.01); *A61K 8/062* (2013.01); *A61K 8/22* (2013.01); *A61K 9/0014* (2013.01); *A61K 9/1075* (2013.01); *A61K 31/05* (2013.01); *A61K 31/07* (2013.01); *A61K 33/40* (2013.01); *A61K 47/10* (2013.01); *A61K 47/26* (2013.01); *A61Q 17/005* (2013.01); *A61K 2800/21* (2013.01)

(58) Field of Classification Search
CPC ...... A61K 9/014; A61K 9/1075; A61K 47/10; A61K 47/26; A61K 31/05; A61K 31/07; A61K 33/40; A61Q 17/005; A01N 59/00
See application file for complete search history.

(56) References Cited

U.S. PATENT DOCUMENTS

| | | | |
|---|---|---|---|
| 4,844,886 A | 7/1989 | Hartmann et al. | |
| 8,114,389 B2 | 2/2012 | Douin et al. | |
| 9,072,917 B2* | 7/2015 | Kawa | A61K 8/37 |
| 2008/0194518 A1* | 8/2008 | Mookerjee | A01N 27/00 514/55 |
| 2009/0130153 A1 | 5/2009 | Issberner et al. | |
| 2009/0143477 A1* | 6/2009 | Baker, Jr. | A61K 8/062 514/642 |
| 2010/0215701 A1 | 8/2010 | Loyen | |

FOREIGN PATENT DOCUMENTS

| | | |
|---|---|---|
| JP | 2001518944 | 10/2001 |
| JP | 200546841 | 2/2005 |
| JP | 2005514325 | 5/2005 |
| JP | 2010523631 | 7/2010 |
| WO | 9855098 | 12/1998 |
| WO | 03000243 A1 | 1/2003 |
| WO | 2008/073684 | 6/2008 |
| WO | 2009132342 A1 | 10/2009 |
| WO | 2009/137100 | 11/2009 |
| WO | 2009/158687 | 12/2009 |
| WO | 2010080438 A2 | 7/2010 |

OTHER PUBLICATIONS

The International Search Report and Written Opinion dated Dec. 22, 2011 for International Application No. PCT/EP2011/053100.
Bowen, P. "Particle Size Distribution Measurement from Millimeters to Nanometers and from Rods to Platelets." Journal of Dispersion Science and Technology. vol. 23, No. 5. 2002. pp. 631-662.
Voegeli, D. "The Role of Emollients in the Care of Patients with Dry Skin." Nursing Standard. vol. 22, No. 7. 2007. pp. 62-68.
English Translation of Notice of Reasons for Rejection; JP N0.: 2013-555767; 3 pages; dated Feb. 2, 2015.

\* cited by examiner

*Primary Examiner* — Nannette Holloman
(74) *Attorney, Agent, or Firm* — Quarles & Brady LLP

(57) ABSTRACT

The present invention provides a chemical composition comprised of hydrogen peroxide and a nanoemulsion of long-chained alcohols which in combination these constituents act synergistically boost the kill-time rate of hydrogen peroxide. The peroxide based nanoemulsion formulation for application to skin includes a cosmetically approved peroxide containing compound present in a range to give from about 0.1 to about 4 wt./wt. % released hydrogen peroxide, an organic acid present in a concentration from about 0.01 to about 5 wt./wt. % for adjusting a pH of the formulation in a range from about pH 1 to about pH 4, a long-chained (C9 to C22) aryl and/or alkyl alcohol, present in a concentration from about 0.1 to about 20 wt./wt. %, and an emollient present in a concentration from about 0.1 to about 40 wt./wt. %, and an emulsifier present in a concentration from about 0.1 to about 20 wt./wt. % to render the formulation a nanoemulsion.

19 Claims, 1 Drawing Sheet

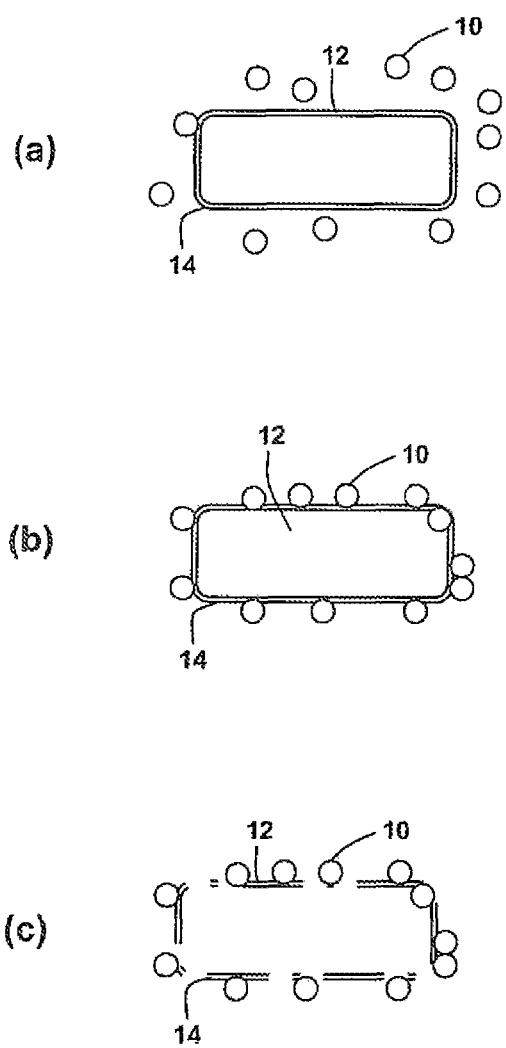

CHEMICAL COMPOSITION WITH HYDROGEN PEROXIDE AND A NANOEMULSION OF LONG-CHAINED ALCOHOLS

CROSS-REFERENCE TO RELATED APPLICATIONS

This application is a National Stage entry of International Application No. PCT/EP2011/053100, filed Mar. 2, 2011, the entire disclosure of which application is incorporated herein by reference.

FIELD OF THE INVENTION

The present invention relates to a very fast-acting and mild to the skin chemical formulation which involves hydrogen peroxide and a micro- or a nanoemulsion of long-chained alcohols and shows antimicrobial activity.

BACKGROUND TO THE INVENTION

Hydrogen Peroxide is a nature's own disinfectant. It is naturally present in milk, honey and in human saliva and tissues as a result of cellular metabolism. It is thus a germicide, with broad spectrum antimicrobial activity, which helps the outer defences of the body as non-immune system. Hydrogen Peroxide kills the pathogenic microorganisms phagocyted by the leucocytes (white cells). The white cells are themselves protected from the hydrogen peroxide by natural antioxidant molecules such as Super Oxide Dismutase, Glutathione (GHS) and Catalase (peroxidase).

The mechanism of action of Hydrogen Peroxide is based on the production of oxygenated free-radicals such as Superoxide anion ($O_2^{\circ-}$) and Hydroxyl radical ($OH^\circ$). These very unstable molecules react extremely quickly with the microorganisms' cell-wall, cell membrane, DNA and enzymes, causing irreversible damage. However, this process is quite slow and the kill-time rate of hydrogen peroxide cannot be considered as fast enough for skin hygiene purposes. For instance, it may take at least 30 minutes for a disinfectant to disinfect a surface.

Combinations of hydrogen peroxide with various stabilizers (chelating agents, acids) and bug-killing boosters (organic acids, surfactants) are known. For instance, N. Omidbakhsh, in U.S. Pat. No. 6,346,279, discloses the concept of "Accelerated Hydrogen Peroxide" (AHP) as following:

An acidic aqueous hydrogen peroxide solution is provided, with improved disinfectant activity. Concentrated solutions preferably contain up to about 8% and as-used concentrations contain about 0.5% peroxide. The solution also contains from 0.1 to 5.0% of at least one acid compound, e.g. phosphoric and/or a phosphonate with from 1 to 5 phosphonic acid groups, and from 0.02 to 5% of at least one anionic surfactant. The surfactant is selected from C8 to C16-alkyl aryl sulphonic acids, sulphonated C12 to C22 carboxylic acids, C8 to C22-alkyl diphenyl oxide sulphonic acids, naphthalene sulphonic acids, C8 to C22 alkyl sulphonic acids, and alkali metal and ammonium salts thereof, and alkali metal C8 to C18 alkyl sulphates, and mixtures thereof. Most preferably the solution has an emulsifier, e.g. a salt of an alkylated diphenyl oxide. The solution may also contain corrosion inhibitors and/or lower alcohols."

The above formulation involves phosphor-containing ingredients which cannot be considered as environmental friendly. It also requires a significant number of bacterial-killing boosters, leading to less biodegradable formulations.

It would therefore be advantageous to provide peroxide containing formulations which boost the kill-time rate of hydrogen peroxide which does not contain environmentally problematic constituents and is readily biodegradable.

SUMMARY OF THE INVENTION

The inventors have discovered a way to synergistically boost the kill-time rate of hydrogen peroxide by dispensing it as part of a nanoemulsion formulation.

The present invention provides a chemical composition comprised of hydrogen peroxide in a nanoemulsion of long-chained alcohols which in combination these constituents act synergistically boost the kill-time rate of hydrogen peroxide. Without being limited to any theory, it is believed that a high-energy state is formed in the nanoemulsion particles when manufactured using either a mechanical means (high-speed mixer) or chemical means (chemical types and ratio of nanoemulsion-forming surfactants).

The active ingredient and the emulsification's high energy level are believed to be important for the antimicrobial mechanism of action. The obtained emulsions are fluid in consistency and milky in appearance. If desired, additional thickeners may be added to increase its viscosity and prevent running in specific applications.

Accordingly the present invention provides a peroxide based nanoemulsion formulation for application to skin, comprising:

at least one peroxide containing compound present in a range to give from about 0.1 to about 4 wt./wt. % released hydrogen peroxide;

at least one organic acid present in a concentration from about 0.01 to about 5 wt./wt. % for adjusting a pH of the formulation in a range from about pH 1 to about pH 4;

at least one long-chained (C9 to C22) aryl and/or alkyl alcohol, present in a concentration from about 0.1 to about 20 wt./wt. %;

at least one emollient present in a concentration from about 0.1 to about 40 wt./wt. %;

water present in an amount sufficient to obtain a nanoemulsion and at least one non-ionic and/or anionic emulsifier present in a concentration from about 0.1 to about 20 wt./wt. %, thus rendering the formulation a nanoemulsion.

A further understanding of the functional and advantageous aspects of the invention can be realized by reference to the following detailed description and drawings.

BRIEF DESCRIPTION OF THE DRAWINGS

Preferred embodiments of the invention will now be described, by way of example only, with reference to the drawings, in which:

FIG. 1 is a diagrammatic representation of the process of pathogen destruction using the compositions disclosed: (a) nanomicelles in contact with a bacteria; (b) nanomicelles fuse with the bacterial cell wall; (c) bacterial cell wall and membrane disrupt, killing the cell.

DETAILED DESCRIPTION OF THE INVENTION

Generally speaking, the embodiments described herein are directed to chemical formulations comprised of emulsions containing peroxide based compounds and long-chained alcohols. As required, embodiments of the present invention are disclosed herein. However, the disclosed embodiments are merely exemplary, and it should be understood that the invention may be embodied in many various and alternative forms. The figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, chemical formulations comprised of emulsions containing peroxide based compounds and long-chained alcohols are disclosed.

As used herein, the terms "about", and "approximately" when used in conjunction with ranges of dimensions, concentrations, temperatures or other physical properties or characteristics is meant to cover slight variations that may exist in the upper and lower limits of the ranges of properties/characteristics.

The present invention provides a nanoemulsion of long-chained alcohols containing a peroxide containing compound. This combination of constituents act synergistically boost the kill-time rate of the peroxide. Without being limited to any theory, it is believed that a high-energy state is formed in the nanoemulsion particles when manufactured using either a mechanical means (high-speed mixer) or chemical means (chemical types and ratio of nanoemulsion-forming surfactants).

Embodiments of the composition include at least one physiologically acceptable, cosmetically approved peroxide compound such as, but not limited to, hydrogen peroxide, calcium peroxide, magnesium peroxide, sodium carbonate peroxide, magnesium peroxide, strontium peroxide, urea peroxide, zinc peroxide. Cosmetically approved peroxide compounds are those authorised by the current cosmetic regulations (i.e. European Cosmetic Directive 76/768/EC).

The peroxides are present in a concentration (released hydrogen peroxide) from about 0.1 wt./wt. % to about 4 wt./wt. %. When the peroxide containing compounds (formed of mother molecules) are dissolved in water they release hydrogen peroxide. The peroxide containing compounds decompose slowly, releasing x moles of linked hydrogen peroxide per mole of "mother molecule".

The compositions may also include at least one non-ionic and/or anionic emulsifier; more specifically, ethoxylated C8 to C22 straight or branched fatty alcohols or fatty acids. It also may include at least one C8 to C22 fatty acid ester and/or at least one C8 to C22 fatty alcohol, or any combination thereof.

Exemplary emulsifiers include Sucrose Polystearate, Beheneth-10 to 25, Oleth-5 to 30, Sodium Stearoyl Glutamate, Sorbitan monolaurate, Lauryl Glucoside, Polyglyceryl-2 Dipolyhydroxystearate, in a concentration from 0.1 to 20 wt./wt. %. Preferred emulsifiers are Ceteareth-20, Ceteareth-30, Glyceryl Stearate, and Ceteareth-12, or any combination thereof.

A preferred emulsifier combination includes each of Ceteareth-20, Ceteareth-30, Glyceryl Stearate, and Ceteareth-12 together which give good results.

The compositions also include at least one organic acid for example propanoic, butanoic, pentanoic, hexanoic, heptanoic, octanioc mono-, di- and tri-acids, or any combination thereof), for adjusting the final pH. Exemplary organic acids include alpha-hydroxy-acids, beta-hydroxy-acids, maleic acid and/or gluconic acid, in a concentration from about 0.01 wt./wt. % to about 5 wt./wt. %. The final pH of the formulation is preferably from about pH 1 to about pH 4, more particularly from about pH 2 to about pH 3. Formulations with a pH in the range 2 to 3 is well tolerated by the skin as long as it is not induced by strong acids (at a given pH, they release more corrosive $H^+$ than weak acids). This low pH also considerably helps the bacteria-killing effectiveness of hydrogen peroxide. Both pKa and concentration of the acids determine the final pH of the formulation.

The compositions may include at least one long-chained aryl and/or alkyl alcohol (C9 to C22) such as, but not limited to Bisabolol, and/or Farnesol and/or Nerolidol, or any combination thereof. A preferred alkyl alcohol is Nerolidol. The long-chained aryl and/or alkyl alcohol is preferably present in a concentration from about 0.1 to about 20 wt./wt. %. High concentrations of liphophilic ingredients are often necessary to obtain micro- and nano-emulsions. This is due to physico-chemical interactions between lipophilic and hydrophilic ingredients, and emulsifiers.

The compositions may include at least one emollient such as, but not limited to Cetearyl isononanoate, Diethylhexylcyclohexane, Hexyldecyl Laurate, Hexyldecanol, Dicaprylyl Ether, Caprylic/capric acid ester, Coco-Caprylate/Caprate, in a concentration from 0.1 to 40 wt./wt. % Preferred emollients are Cetearyl alcohol, Lauric acid hexylester, coco-caprylate/caprate, cetostearyl isononanoate, decyl oleate, dethylhexylcyclohexane, dicaprylyl ether. A most preferred emollient is Cetearyl isononanoate.

The emollient may be present in a concentration from about 0.1 wt./wt. % to about 40 wt./wt. %. High concentrations of liphophilic ingredients are often useful to obtain micro- and nano-emulsions. Also, a high concentration is preferred to provide the formulation with significant sensory properties.

The formulations provided herein include a sufficient amount of water ($H_2O$) present in an amount sufficient to obtain the nanoemulsion. The range of concentration of water present in the formulation may be from about 20 wt./wt. % to about 95 wt./wt. %.

The active ingredient and the emulsification's high energy level are believed to be important for the antimicrobial mechanism of action. The obtained emulsions are milky in consistency and appearance. If desired, additional thickeners could be added to increase its viscosity and prevent running in specific applications.

The nanoemulsion particles are thermodynamically driven to fuse with lipid-containing organisms. This fusion may be enhanced by the electrostatic attraction between the eventual cationic charge of the emulsion and the anionic charge on the pathogen. When enough nanoparticles fuse with the pathogens, they release part of the energy trapped within the emulsion. Both the active ingredient and the energy released destabilize the pathogen lipid membrane, resulting in cell lysis and death (see FIG. 1). FIG. 1(a) shows nanomicelles 10 in contact with a bacteria cell 12; (b) shows the nanomicelles 10 fusing with the bacterial cell wall 14; (c) shows the bacterial membrane/cell wall 14 and membrane disrupting, thus killing the cell 12.

A unique aspect of the nanoemulsions is their selective toxicity to microbes at concentrations that are non-irritating to skin. The safety margin of the nanoemulsion is due to the low level of emulsifier in each droplet.

The nanoemulsion may be obtained by Temperature Inversion Phase (PIT) or using high-pressure equipment (i.e. 'high-pressure homogenizer/piston homogenizer', 'microfluidizer') or using 'Ultrasonification', and optimized in order to show shear thinning rheological Newtonian behaviour and low viscosity (less than 100 mPas) which guaranties a good sprayability. Nanoemulsions may be defined as oil-in-water (o/w) emulsions with mean droplet diameters ranging from 50 to 1000 nm. Usually, the average droplet size is between about 100 to about 500 nm. A preferred droplet size of the droplets forming the present nanoemulsion is in a range from about 0.1 to about 0.3 micrometer.

The emulsions disclosed herein, when combined with hydrogen peroxide, shows significant bactericidal activity on Gram positive (*Bacillus, Staphylococcus aureus, Enterococcus feacalis, Streptococcus pyogenes, Listeria monocytogenes, Clostridium difficile*) and Gram negative (*Pseudomonas aeruginosa, Escherichia Serratia marscens, Salmonella enterolytica, Salmonella typhi*) bacteria as well as yeasts (*Candida albicans*) and moulds (*Aspergillus niger*).

The inventors have discovered that by combining a peroxide compound which decomposes to hydrogen peroxide with a long-chained alcohol provides a formulation having optimised antimicrobial properties. Again, without being bound by any theory, the inventors contemplate that by microionizing the alcohol acts to increase its affinity for the bacterial structures and is eventually be passively absorbed by the micro-organisms which is believed to kill them instantly.

The formulations disclosed herein are very advantageous because they require very small quantities of the various ingredients, thus providing very cost-effective and non-toxic new type of skin disinfectant.

As used herein, the terms "comprises", "comprising", "includes" and "including" are to be construed as being inclusive and open ended, and not exclusive. Specifically, when used in this specification including claims, the terms "comprises", "comprising", "includes" and "including" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. A peroxide based antimicrobial formulation comprising a nanoemulsion for application to skin for disinfection thereof, wherein the nanoemulsion comprises:
   at least one peroxide containing compound present in a range to give from about 0.1 to about 4 wt./wt. % released hydrogen peroxide;
   at least one organic acid present in a concentration from about 0.01 to about 5 wt./wt. % for adjusting a pH of the formulation in a range from about pH 1 to about pH 4;
   at least one long-chained (C9 to C22) aryl and/or alkyl alcohol, present in a concentration from about 0.1 to about 20 wt./wt. %;
   at least one emollient present in a concentration from about 0.1 to about 40 wt./wt. %;
   at least one emulsifier present in a concentration from about 0.1 to about 20 wt./wt. %, wherein the emulsifier comprises an anionic emulsifier, and
   water present in a concentration from about 20 wt./wt. % to about 95 wt./wt. %.

2. The formulation according to claim 1 wherein said at least one peroxide containing compound is selected from the group consisting of hydrogen peroxide, calcium peroxide, magnesium peroxide, sodium carbonate peroxide, magnesium peroxide, strontium peroxide, urea peroxide, and zinc peroxide, and any combination thereof.

3. The formulation according to claim 1 wherein said at least one peroxide containing compound is hydrogen peroxide.

4. The formulation according to claim 1 wherein said at least one emulsifier further comprises a non-ionic emulsifier selected from the group consisting of ethoxylated C8 to C22 straight or branched fatty alcohols, ethoxylated C8 to C22 straight or branched fatty acids, C8 to C22 fatty acid esters, C8 to C22 fatty alcohols, and any combination thereof.

5. The formulation according to claim 1 wherein said anionic emulsifier is sodium stearoyl glutamate.

6. The formulation according to claim 1 wherein said at least one emulsifier further comprises a non-ionic emulsifier selected from the group consisting of ceteareth 20, ceteareth-30, glyceryl Stearate, ceteareth-12, and any combination thereof.

7. The formulation according to claim 6 wherein said emulsifier is a combination of ceteareth-20, ceteareth-30, glyceryl Stearate and ceteareth-12.

8. The formulation according to claim 1 wherein said at least one organic acid is selected from the group consisting of propanoic, butanoic, pentanoic, hexanoic, heptanoic, octanioc mono-, di- and tri-acids, and any combination thereof.

9. The formulation according to claim 1 wherein said at least one organic acid is selected from the group consisting of alpha-hydroxy-acids, beta-hydroxy-acids, maleic acid and gluconic acid, and any combination thereof.

10. The formulation according to claim 1 wherein said at least one organic acid is maleic acid.

11. The formulation according to claim 1 wherein said at least one long-chained aryl and/or alkyl alcohol is selected from the group consisting of bisabolol, farnesol, nerolidol, and any combination thereof.

12. The formulation according to claim 1 wherein said at least one long-chained aryl and/or alkyl alcohol is nerolidol.

13. The formulation according to claim 1 wherein said at least one emollient is selected from the group consisting of Cetearyl isononanoate, diethylhexylcyclohexane, hexyldecyl laurate, hexyldecanol, dicaprylyl ether, caprylic/capric acid ester, coco-caprylate/caprate, cetearyl alcohol, laurie acid hexylester, coco-caprylate/caprate, cetostearyl isononanoate, decyl oleate, diethylhexylcyclohexane, dicaprylyl ether, paraffin oil, and any combination thereof.

14. The formulation according to claim 1 wherein said at least one emollient is Cetearyl isononanoate.

15. The formulation according to claim 1 wherein said at least one organic acid is selected to adjust the pH of the formulation in a range from about pH 2 to about pH 3.

16. The formulation according to claim 1 wherein said peroxide based nanoemulsion is comprised of droplets having a size in a range from about 0.1 to about 0.3 micrometers.

17. The formulation according to claim 1 produced by temperature inversion phase.

18. The formulation according to claim 1 wherein said at least one emulsifier further comprises a non-ionic emulsifier selected from the group consisting of sucrose polystearate, beheneth-10 to 25, oleth-5 to 30, sorbitan monolaurate, lauryl glucoside, polyglyceryl-2 dipolyhydroxystearate, and any combination thereof.

19. The formulation according to claim 1 wherein said at least one peroxide containing compound is hydrogen peroxide and at least one long-chained aryl and/or alkyl alcohol is nerolidol.

* * * * *

UNITED STATES PATENT AND TRADEMARK OFFICE
CERTIFICATE OF CORRECTION

PATENT NO. : 9,844,216 B2
APPLICATION NO. : 14/002432
DATED : December 19, 2017
INVENTOR(S) : Pierre Grascha et al.

It is certified that error appears in the above-identified patent and that said Letters Patent is hereby corrected as shown below:

In the Specification

Column 5, Line 14, "Escherichia" should be -- Escherichia coli, --.

Signed and Sealed this
Twenty-fourth Day of July, 2018

Andrei Iancu
*Director of the United States Patent and Trademark Office*